United States Patent [19]

Harris

[11] Patent Number: 4,712,557
[45] Date of Patent: Dec. 15, 1987

[54] A PACER INCLUDING A MULTIPLE CONNECTOR ASSEMBLY WITH REMOVABLE WEDGE AND METHOD OF USE

[75] Inventor: Donald L. Harris, Miami, Fla.

[73] Assignee: Cordis Leads, Inc., Miami, Fla.

[21] Appl. No.: 856,484

[22] Filed: Apr. 28, 1986

[51] Int. Cl.⁴ ............................................. A61N 1/36
[52] U.S. Cl. ................................ 128/419 P; 439/86; 439/586; 439/669
[58] Field of Search ........... 128/419 P, 419 C, 419 E, 128/419 R, 419 PS; 339/273 R, 273 F, DIG. 3

[56] References Cited

U.S. PATENT DOCUMENTS

| | | | |
|---|---|---|---|
| 2,107,835 | 2/1938 | Pierce | 339/273 R |
| 3,760,332 | 9/1973 | Berkovits | 128/419 P |
| 3,760,342 | 9/1973 | Prouty et al. | 339/DIG. 3 |
| 3,908,668 | 9/1975 | Bolduc | 128/419 P |
| 4,112,953 | 9/1978 | Shanker et al. | 128/419 P |
| 4,141,752 | 2/1979 | Shipko | 128/419 P |
| 4,142,532 | 3/1979 | Ware | 128/419 P |
| 4,152,540 | 5/1979 | Duncan et al. | 174/152 GM |
| 4,154,248 | 5/1979 | Jones | 128/419 P |
| 4,182,345 | 1/1980 | Grose | 128/419 P |
| 4,202,592 | 5/1980 | Rulier et al. | 128/419 P |
| 4,226,244 | 10/1980 | Coury et al. | 128/419 P |
| 4,236,525 | 12/1980 | Sleutz et al. | 128/419 P |
| 4,262,982 | 4/1981 | Kenny | 128/419 P |
| 4,445,511 | 5/1984 | Cowdery et al. | 128/419 P |
| 4,469,104 | 9/1984 | Peers-Trevarton | 128/419 P |
| 4,603,696 | 8/1986 | Cross, Jr. et al. | 128/419 P |

Primary Examiner—William E. Kamm
Attorney, Agent, or Firm—Henry W. Collins; Thomas R. Vigil

[57] ABSTRACT

A connector assembly for use in a cardiac pacer system comprising a cardiac pacer including a pacer case having a top wall and a pacing lead having a distal end, a distal end portion, a proximal end and a proximal end portion with at least one connector band mounted on said proximal end portion. A neck assembly is mounted to the top wall of the pacer case. The connector assembly comprises an elastomeric neck mounted on the top wall of the pacer case and forms part of the neck assembly. The neck has a lumen therein for receiving the proximal end portion of the pacing lead. A resilient conductive member is mounted in the neck and is positioned to contact the connector band on the proximal end portion of the lead received in the lumen. The neck assembly further includes a removable wedge for urging the resilient conductive member against the connector band.

24 Claims, 8 Drawing Figures

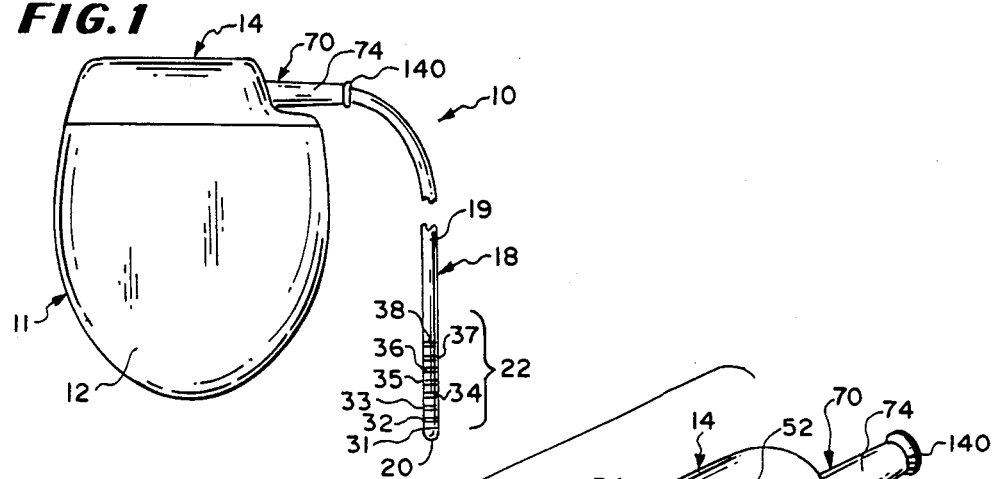
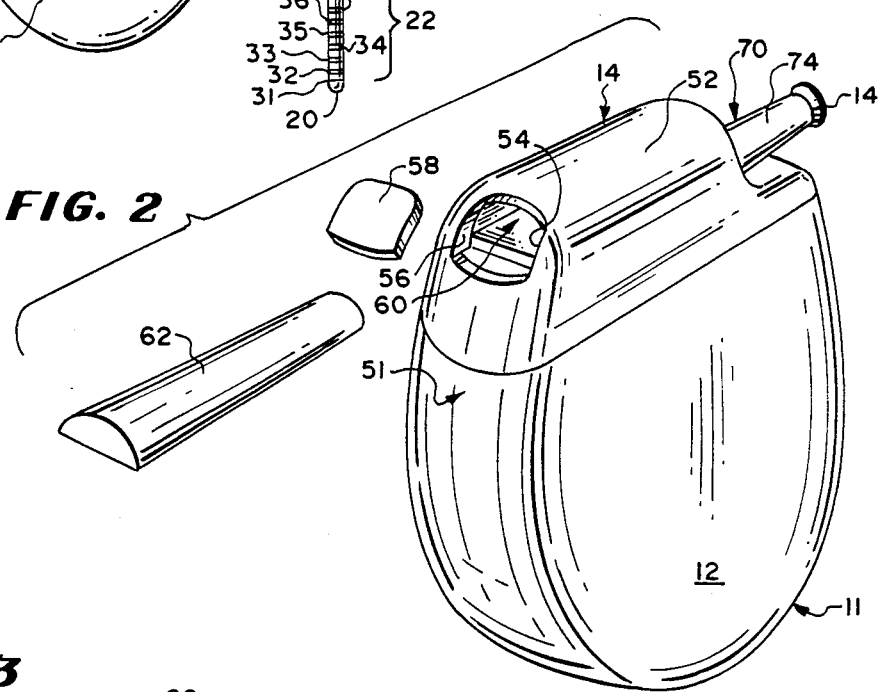
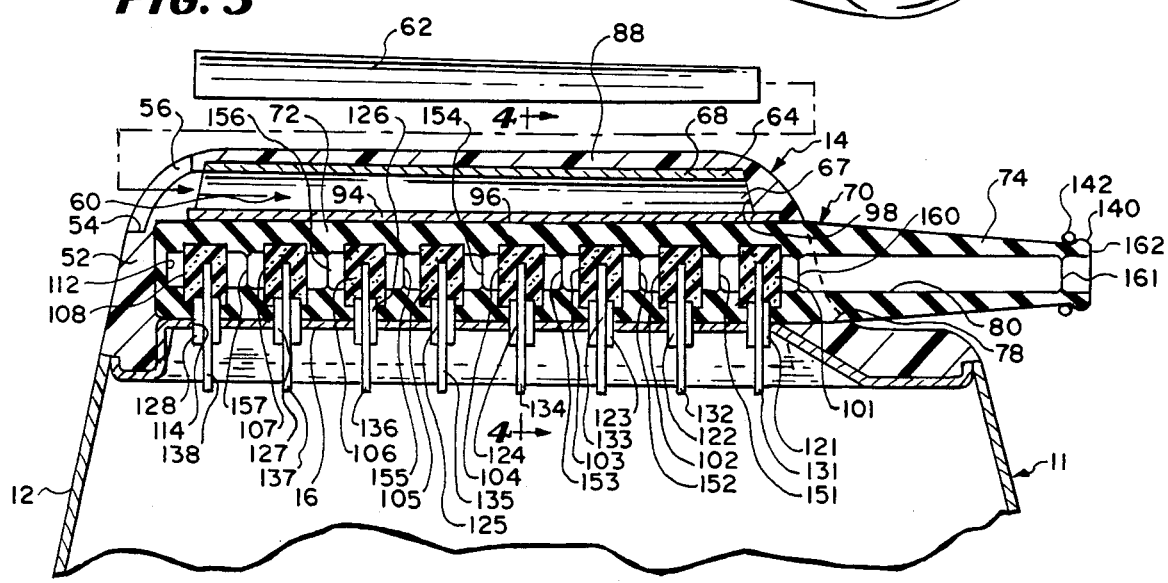

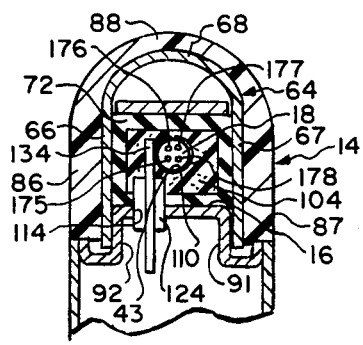
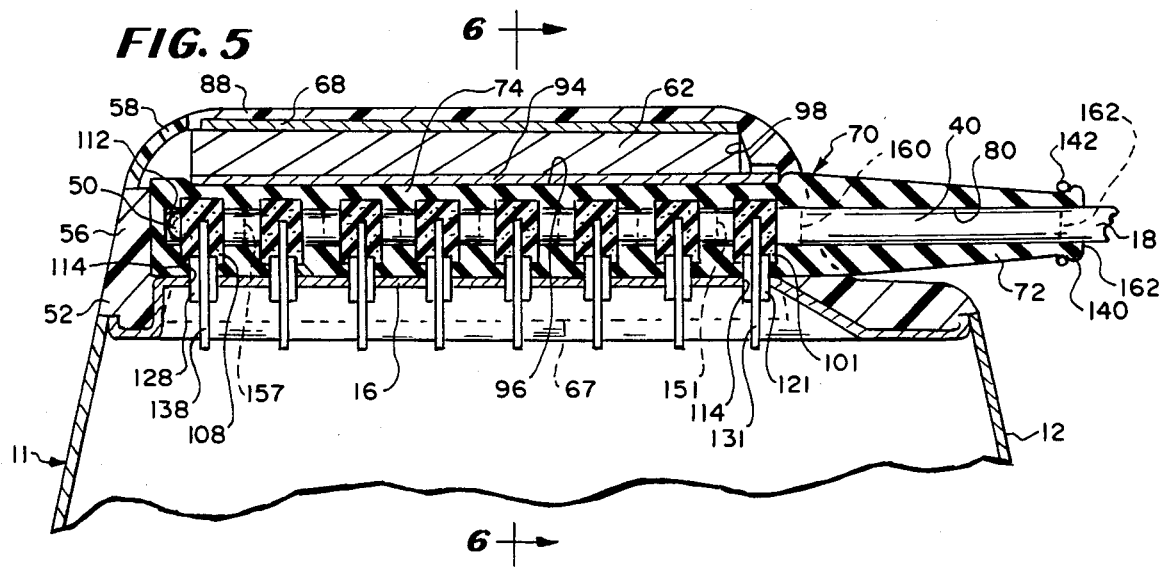
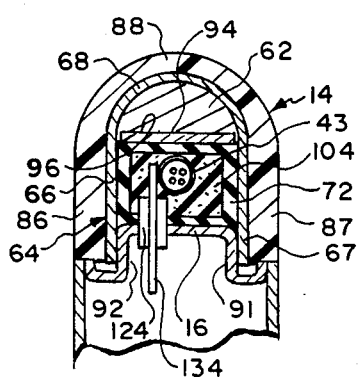
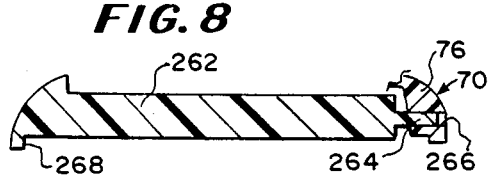
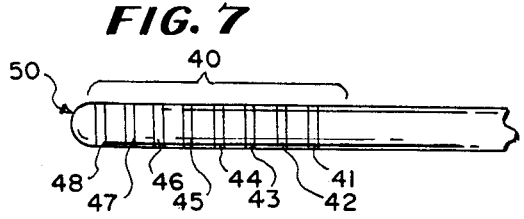
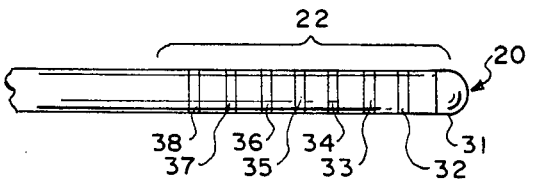

A PACER INCLUDING A MULTIPLE CONNECTOR ASSEMBLY WITH REMOVABLE WEDGE AND METHOD OF USE

BACKGROUND OF THE INVENTION

Field of the Invention

The present invention relates to a pacer connector assembly for connecting a cardiac pacing lead to a pacer, and more particularly to a pacer connector assembly which readily connects with the proximal end of an in-line multielectrode pacing lead. The connector assembly is designed to be expandable to accommodate and connect with a plurality of connector bands on the proximal end portion of the pacing lead and includes a soft, pliable, so-called pacer neck which has a socket for receiving the proximal end of the pacing lead. The assembly further includes spaced apart conductive elastomeric connectors in the neck and a removable wedge for squeezing the connectors against the connector bands on the pacing lead.

Description of the Prior Art

A pacing system includes a pacer, which comprises a metal container or case that contains electronic circuitry and a power supply, and a pacing lead. The proximal end of the lead is connected to output terminals of the pacer in a component of the pacer which is commonly referred to as the neck of the pacer mounted to a top side of the case.

Multiple eletrode cardiac pacing leads are well known and have been utilized for pacing both the atrial and ventricular chambers of the heart. Such a pacing lead includes a multipolar electrode assembly at the distal end and terminal connector bands or rings at the proximal end. The multipolar electrodes at the distal end of the lead usually comprise a tip electrode and one or more ring electrodes along the length of the lead. Additionally, the lead may contain one or more sensors along its length which measure and monitor physiological parameters such as, for example, ejection time, pressure of blood in a ventricle or the partial pressure of oxygen or carbon dioxide within the chambers of the heart.

In a pacing system with one electrode on the pacing lead, the distal end or tip of the lead contains the electrode and is usually placed in the ventricle of the heart. The electrode is connected to the lead by an insulated helically coiled wire conductor. At the proximal end of the lead, a terminal pin is affixed to the lead. This pin is inserted into a socket in the pacer neck where it makes contact with an electrical connector socket which is, in turn, connected to cardiac pacer electronic circuitry and a power source in the pacer case.

With one electrode on the distal end of the lead, the pacer system is referred to as a unipolar system. Then one pacer lead connector is needed in the neck of the pacer to serve as a cathode connector, with the case or can of the pacer, which is normally metal, serving as an anode. In a bipolar system, where two electrodes are on the distal end of the lead, a pacing lead terminal pin and terminal connector band are provided on the proximal end of the lead and two pacer lead connectors are necesssary in the neck of the pacer.

Currently, cardiac pacing sytstems focus upon (a) the sensing of electrical signals generated by the myocardium or middle layer of the atrial and/or ventricular chambers of the heart and (b) the stimulation of one or both of these chambers in the absence of spontaneous electrical activity. In such a dual chamber system, either two different leads are used or the lead used measures ventricular activity at its tip and atrial activity along its length and therefore, more than one connector is needed in the pacer neck. In dual chamber unipolar systems, two pacer lead connectors are required in the neck of the pacer, one for the atrial lead terminal connector pin or band and one for the ventricular lead terminal connector pin or band. In a bipolar dual chamber system, four pacer lead connectors are required in the pacer neck for connecting to pacing lead proximal terminal connectors, such as a terminal pin and three connector bands for monitoring both chambers of the heart.

Future pacing systems will include physiological sensors, either as part of the pacing lead or separate from it. These physiological sensors will measure parameters such as oxygen or carbon dioxide levels in the blood, ventricular blood pressure, ejection time, pH, or any combination thereof, to name a few. These parameters will be transmitted to the pacer circuitry for use in setting various pacer outputs. Additionally, each of these sensors will require an electrical contact or connector within the pacer neck in addition to the contacts or connectors described above for connection to the electrodes for sensing electrical activity.

Multielectrode pacing leads most suitable for this type of electrode and sensor system include a lead with multiple ring electrodes and sensors on the distal end and multiple spaced apart connector bands on the proximal end of the lead in an in-line arrangement and isodiametric with the lead. Such a lead allows the monitoring of several different parameters while only causing one insertion to be made into the heart which reduces trauma. An example of such a lead is disclosed in U.S. Pat. No. 4,469,104 which discloses a lead assembly for a body implantable tissue stimulator which contains a connector system of a terminal electrode assembly on the proximal end of the lead and a connector assemby in the pacer neck which relies on garter springs or conductive elastic O-rings to contact each, in-line spaced apart connector band or ring on the proximal end of the lead. Although such a lead is effective, the connectors used are hard to manufacture, are difficult to insert into the pacer neck and are too large to accommodate a large number of connector bands within the minute confines of the pacer neck.

Heretofore various connectors have been utilized for connecting the proximal end of a single or multielectrode pacing lead to the electrical outputs in the neck of a pacer. The most common type of connector system employs a terminal pin on the proximal end of the pacing lead which is secured inside the neck to a connector of the pacer by a set screw. This arrangement is not completely desirable since it usually requires the surgeon to tighten the screw after the terminal pin of the lead is in place inside the neck of the pacer during implantation in a body. Such a procedure is complicated due to the small size of the screw and the conditions of the operating room.

Additionally, the number of terminal connector bands or rings on multielectrode lead is restricted if a different set screw is needed in the connector assembly for each terminal connector band or ring on the pacing lead. Present connector assemblies which employ set screws are limited to a maximum of four set screw connectors for four pacing lead terminal connectors, e.g., a pin and three bands, due to the size limitations of the pacer neck.

Finally, the set screws encounter problems with body fluids over an extended period of time which cause deterioration of a screw and entry of fluid into the electrical contact area causing damage and malfunction. In some pacer systems, a cap has been used to cover the screw head but such a system has not been entirely effective and has further complicated the pacer installation procedure.

Therefore, the need exists for a multiple contact connector assembly in a pacer neck which is small in size, easy to manufacture, readily accommodates a multielectrode lead, is impervious to body fluids and can be adapted to receive and make contact with a number of connector bands or rings on the lead, the number being variable and dependent upon the number of distal electrodes and sensors required for a particular patient.

As will be described in greater detail hereinafter, the assembly of the present invention provides a device which is capable of readily accommodating the proximal end portion of an in-line multielectrode lead without any additional complex installation procedures and is completely sealed from the body it is implanted in.

Moreover, the connector assemby of the present invention differs from previously proposed connector assemblies and pacer neck constructions by providing a connector assembly and pacer neck construction which is small in size, contains its own lead strain relief, is easy to use, can accommodate a large number of terminal connector bands, provides removable means for placing pressure against the contacts or connectors engaging the connector bands on a pacing lead, is easy to manufacture, and which maintains high reliability of electrical contact between each assembly connector/connector band connection throughout the life of the pacing system.

SUMMARY OF THE INVENTION

According to the invention there is provided a pacer including a multiple connector assembly for use in a cardiac pacing system including: a pacer case having a top wall and pulse generating means enclosed therein, a pacing lead with a plurality of connector bands mounted on the proximal end portion of the lead and a neck assembly mounted to the top wall of the pacer case. A connector assembly compring an elastomeric neck is mounted on the top wall of the pacer case and forms a part of the neck assembly. The neck has a lumen therein to receive the proximal end portion of the pacing lead. Within the neck there is a plurality of resilient conductive means in registry with a respective number of connector bands on the proximal end portion of the lead when the lead is positioned in the lumen. The neck assembly further includes a movable member for urging the resilient conductive means against the connector bands to provide electrical continuity between the pulse generating means and the pacing lead.

Further according to the invention there is provided a method for connecting the pacing lead proximal end to the conductor assembly including the steps of: removing the movable member urging means from a space in the neck assembly above the elastomeric neck, inserting the proximal end of the pacing lead into the lumen until the connector bands are in registry with the respective conductive means and inserting the movable member urging means through an opening in the neck assembly into the space in the neck assembly to urge the resilient conductive means against the connector bands.

BRIEF DESCRIPTION OF THE DRAWINGS

FIG. 1 is a side view plan view of a pacer system including a pacer and a multielectrode pacing lead both constructed according to the teachings of the present invention.

FIG. 2 is a perspective view of the cardiac pacer shown in FIG. 1 viewing same from a back corner thereof and shows a wedge, a plug for an opening in a pacer neck assembly and the pacer exploded.

FIG. 3 is a vertical longitudinal sectional view of the pacer neck assembly including the connector assembly of the present invention with the wedge removed.

FIG. 4 is a vertical sectional view of the pacer neck assembly with the wedge removed as shown in FIG. 3 and is taken along line 4—4 of FIG. 3.

FIG. 5 is a vertical longitudinal sectional view of the pacer neck assembly similar to the view shown in FIG. 5 but with the wedge inserted in the assembly.

FIG. 6 is a vertical sectional view of the pacer neck assembly shown in FIG. 5 and is taken along line 6—6 of FIG. 5.

FIG. 7 is a plan view of the multielectrode pacing lead with a middle portion thereof broken away.

FIG. 8 is a longitudinal sectional view through a modified embodiment of the wedge.

DESCRIPTION OF THE PREFERRED EMBODIMENT

Referring now to the drawings in greater detail, there is illustrated in FIG. 1 a pacer system 10 comprising a cardiac pacer 11 including a pacer case 12 and a pacer neck assembly 14 mounted on a top side 16 (FIG. 3) of the pacer case 12. The pacer case 12 is typically made of metal.

The pacer system 10 further includes a pacing lead 18 which includes a lead body 19, which has a distal end 20, a distal end portion 22 mounting a plurality of electrodes or sensors 31–38, and a proximal end portion 40 (hidden from view in FIG. 1 and shown in FIG. 7), which is adapted to be received in the pacer neck assembly 14.

Turning now to FIG. 7 it will be apparent that the pacing lead distal end portion 20 includes a tip electrode 31 and, in the illustrated embodiment, seven ring electrodes or sensors 32–38. Then, the proximal end portion 40 of the pacing lead 18 has eight spaced apart connector bands 41–48 thereon which are connected to various ones of the electrodes and sensors 31–38 and a proximal end 50.

The ring electrodes or sensors 31–38 and the connector bands 41–48 are preferably isodiametric with the pacing lead body 19.

In accordance with the teachings of the present invention and as shown in an exploded perspective view of back side 51 of the pacer 11 in FIG. 2, the pacer neck assembly 14 includes a cap 52 with an opening 54 in a rear end wall 56 thereof, a removable plug 58 which is shaped to fit in the opening 54 and a space 60 within the cap 52 communicating, i.e., in registry, with the opening 54 and into which an elongate metal wedge member 62 can be inserted for a purpose which will be explained below in connection with the description of FIGS. 3–6.

Turning now to FIG. 3, the pacer neck assembly 14 includes the cap 52 which is preferably made of a molded epoxy material and which is molded about an elongate metal hood member 64 (FIG. 4) that forms part of the cap 52 and that is fixed to the top wall 16 of the case 12. The hood member 64 has an inverted U-shaped cross-section and includes opposite side walls 66 and 67 and a rounded top wall 68.

The pacer neck assembly 14 further includes an elongate elastomeric neck 70 which is received between the side walls 66 and 67 of the hood member 64. The elastomeric neck 70 includes a elongate main body portion 72 which is received within the cap 52 and a snout portion 74 which extends from a front end wall 76 of the cap 52 through an opening 78 in the front wall 76. The elastomeric neck 70 has a lumen 80 therein which extends through the snout portion 74 and the main body portion 72 and which is sized to receive the proximal end portion 40 of the pacing lead 18 therein.

As shown in FIG. 4, the cap 52 includes epoxy side wall portions 86 and 87 intergral with a rounded top wall portion 88 which are molded about the hood member 64 which reinforces the cap 52 as shown in FIG. 4. The lower portions of the side walls 66 and 67 are fixed (such as by welding) to offset flange portions 91 and 92 of the top wall 16 of the pacer case 12.

As shown in FIGS. 3 and 4, the main body portion 72 is generally rectangular in cross-section with the lumen 80 formed therein and with a elongate metal slate 94 received in the space 60 between the top wall 68 and an upper elongate outer flat surface 96 of the elastomeric neck 70. The space has the general shape of a "half moon". Likewise, the wedge member 62 has the general shape of a "half moon" and has a thickness slightly greater than the top-to-bottom extent of the space 60. Also, if desired, the space 60 and the wedge member 62 can taper from a smaller cross-section extent at an inner end 98 of the space 60 to a larger cross-sectional extent at the opening 54.

Mounted within the elastomeric neck 70 when the neck is molded from an elastomeric material such as polyurethane or Silastic TM are a plurality of, and in the illustrated embodiment, eight elastomeric blocks 101-108, each of which has a hole 110 therein as shown in FIG. 4. The proximal end portion 40 of the pacing lead 18 is received through the holes 110 when the wedge member 62 is removed and the pacing lead is inserted into the lumen 80. The blocks 101-108 can also be made of polyurethane or Silastic TM with a conductive material therein.

Referring to FIG. 5, it will be understood that the spacing between the conductive elastomeric blocks 101-108 in the main body portion 72 of the elastomeric neck 70 is equivalent to the spacing between the connector bands 41-48 on the proximal end portion 40 of the pacing lead 18 so that when the proximal end 50 of the lead 18 is inserted into the lumen 80 and bottoms or engages an inner closed end 112 of the lumen 80, the connector bands 41-48 will be in registry with, and received in, the holes 110 in the conductive elastomeric blocks 101-108.

To facilitate the insertion of the proximal end portion 40 of the lead 18 into the lumen 80, the wedge member 62 is removed as shown in FIG. 3. Then, after the proximal end portion 40 of the lead 18 is received within the lumen 80 and the proximal end 50 bottoms on the inner end 112 of the lumen 80, the wedge member 60 is reinserted into the space 60 as shown in FIG. 5 to apply pressure through the slate 94 to the top surface 96 of the elastomeric neck 70 thereby to force the conductive elastomeric blocks 101-108 against the connector bands 41-48 received therein.

The top wall 16 of the pacer case 12 has a plurality of openings 114 (FIGS. 3 and 4) therein which are received and sealingly mounted, insulated feedthrough members 121-128. Each of the insulated feedthrough members 121-128 has a wire conductor 131-138 extending therethrough. An upper end of each wire conductor 131-138 is embedded in one of the conductive elastomeric blocks 101-108 and a lower end of each wire conductor 131-138 is adapted to be connected to electronic control and pulse generating circuitry mounted within the pacer case 16.

The snout portion 74 of the elastomeric neck 70 in the neck assembly 14 provides strain relief in that it prevents sharp bends of the pacing lead 18 in the area of its entry into the neck assembly 14.

Also, to facilitate further fixing of the pacing lead proximal end portion 40 in the elastomeric neck 70, the snout portion 74 is flared at its outer end to a bead 140 which forms a stop about which a suture 142 can be tied for causing the snout portion 74 to tightly grip the lead 18 in the area of the suture.

Further, to prevent electrical conductive paths from being established between the conductive elastomeric blocks 101-108 annular ribs 151-157 are formed in the neck 70 and in the lumen 80 between each adjacent two conductive elastomeric blocks 101-108. Additionally, an annular rib 160 is provided in the lumen 80 between outer end 162 of the snout portion and the first conductive elastomeric block 101. Preferably, for further sealing, another annular rib 161 is provided in the lumen 80 adjacent the outer end 162 of the snout portion 74 and near the place where the suture 142 is tied about the snout portion 74.

The epoxy, metal hood reinforced, cap 52 is molded about the elongate U-in-cross-section reinforcing hood member 64 that is received about the elastomeric neck 70 and fills the various recessed portions of the top wall 16 of the pacer case 12 to provide the neck assembly 14 with a smooth outer surface which blends with the outer surface of the pacer case 12 as shown in FIGS. 1 and 2.

With the pacer system 10 constructured according to the teachings of the present invention as described above, a multi-electrode pacing lead 18 with in-line electrodes or sensors 31-38 in the distal end portion 22 thereof, such as, for example, a tip electrode 31 for engaging the appex of the ventricle, one or more atrial electrodes for sensing electrical pulses in the atrial wall and one or more sensors, such as a pressure sensor, a $pCO_2$ sensor or $pO_2$ sensor, to name a few, can be mounted in the distal end portion 22. Then electrical wire conductors will extend in a straight or coiled manner through the pacing lead 18 for connection to the connector bands 41-48.

As shown schematically in FIGS. 4 and 6, four conductors 175-178 will extend proximately from the position of the conductor band 44 within the pacing lead proximal end portion 40 either in an insulated coiled manner or in a straight insulated manner (as shown in FIGS. 4 and 6) for connection to the conductor bands 45-48, respectively.

In FIG. 8 is illustrated another embodiment of a wedge 262 which can be used in place of the wedge 62. The wedge 262 is preferably made of a plastic material and has a protrusion or pin 264 at the front end thereof which extends into and if desired through a hole 266 in the front wall 76 of the elastomeric neck 70. The pin 264 facilitates removal of the wedge 262 merely by pushing or pounding on the pin 264.

The rear end of the wedge 262 has a plug formation 268 fixed thereto or formed integral therewith. The plug formation 268 replaces the plug 58 and has a size, shape and contour so as to fit closely or snugly within the opening 54 and provide a smooth continuation of the outer surface of the rear end wall 56.

From the foregoing description it will be apparent that the pacer system 10 of the present invention provides a number of advantages some of which have been described above and others of which are inherent in the invention. Most importantly, the pacer system 10 provides a system whereby proximal end portion 40 of a pacing lead 18 having a plurality of spaced apart connector bands 41-48 can be inserted into the lumen 80 with limited insertion force required, the insertion force required being only that needed to push the pacing lead proximal end portion 40 past the annular ribs 151-157, 160 and 161 and through the holes 110 in the conductive elastomeric blocks 101-108. Then after the pacing lead proximal end portion 40 has been fully inserted into the lumen 80, the elongate wedge member 62 or 262 can be inserted into the space 60 to put pressure on the main body portion 74 of the elastomeric neck 70 thereby to cause the conductive elastomeric blocks 101-108 to grip the connector bands 41-48 on the proximal end portion 40 of the pacing lead 18.

Also, from the foregoing description, it will be apparent that modifications can be made to the pacer system 10 of the present invention without departing from the teachings of the present invention. Accordingly, the scope of the invention is only to be limited as necessitated by the accompanying claims.

I claim:

1. A pacer including a connector assembly for use in a cardiac pacing system comprising:
   a pacer case having a top wall and pulse generating means enclosed therein:
   a pacing lead having a distal end, a distal end portion, a proximal end and a proximal end portion with a plurality of spaced apart connector bands mounted on said proximal end portion;
   a neck assembly mounted to said top wall of said pacer case;
   said connector assembly comprising an elastomeric neck mounted on said top wall of said pacer case and forming part of said neck assembly;
   said neck having a lumen therein for receiving said proximal end portion of said pacing lead;
   a plurality of resilient conductive means in said neck, each of said resilient conductive means being in registry with respective ones of said connector bands on said proximal end portion of said lead when said lead is positioned in said lumen;
   and said neck assembly including removable means for urging said resilient conductive means against said connector bands thereby providing electrical continuity between said pulse generating means and said pacing lead.

2. The connector assembly of claim 1 wherein said neck assembly includes two rigid side walls fixed to said pacer case on either side of said neck, said elastomeric neck having an upper outer surface and said means for urging said resilient conductive means includes means for urging said upper outer surface of said neck downwardly.

3. The connector assembly of claim 2 wherein said neck assembly includes a rigid top wall fixed to said rigid side walls, said top wall being positioned above said upper outer surface of said elastomeric neck to provide a space, and said means for urging said resilient conductive means against said connector bands including a rigid removable wedge member insertable between said side walls into said space between said top wall and said upper outer surface of said elastomeric neck, the top to bottom extent of said space being less than the thickness of said wedge such that said wedge forces said elastomeric neck downwardly.

4. The connector assembly of claim 3 including an elongate rigid slate which is situated on said upper outer surface of said elastomeric neck.

5. The connector assembly of claim 4 wherein said slate is made of metal.

6. The connector assembly of claim 3 wherein said rigid side walls and top walls form a cap for said elastomeric neck which cap is fixed to said top wall of said pacer case.

7. The connector assembly of claim 6 wherein at least a portion of said cap is made of an epoxy material.

8. The connector assembly of claim 7 wherein said cap includes an elongate generally U-in-cross-section metal member which extends over said elastomeric neck and is fixed to said top wall of said case, said epoxy material being placed over said metal member.

9. The connector assembly of claim 8 wherein said space and said wedge have a generally half-moon configuration.

10. The connector assembly of claim 7 wherein said cap has a rear end wall and a front end wall, said front end wall having a first opening therein through which a portion of said elastomeric neck extends and said back end wall having a second opening therein in registry with said space and through which said wedge member is inserted into said space.

11. The connector assembly of claim 10 including a removable plug which is received in and closes off said opening in said rear end wall of said cap.

12. The connector assembly of claim 10 wherein said elastomeric neck is elongate and has an elastomeric main body portion received in said cap and a snout portion which extends outwardly from said cap through said first opening in said front wall of said cap, said snout portion providing strain relief for the pacing lead received therein by preventing sharp bends of the pacing lead at its point of entry into the main body portion of said elastomeric neck, said lumen extending through said elongate main body portion and through said snout portion.

13. The conductor assembly of claim 12 wherein said snout portion is flared at its outer end to provide a lead which facilitates tying of a suture around said snout portion and around said pacing lead when said pacing lead is placed in said lumen in said snout portion.

14. The connector assembly of claim 12 wherein said neck has an annular rib in said lumen positioned between said resilient conductive means and the outer end of said snout portion to prevent liquid from entering into said lumen and contacting said resilient conductive means or said connector band on said lead.

15. The connector assembly of claim 14 wherein said neck has a second annular rib inside said lumen located adjacent the outer end of said snout portion for providing further sealing means for preventing entry of liquid into said lumen.

16. The connector assembly of claim 14 wherein said neck has a plurality of annular ribs in said lumen positioned between each of said resilient conductive means.

17. The connector assembly of claim 3 wherein said wedge is made of metal.

18. The connector assembly of claim 3 wherein said wedge is made of a plastic material.

19. The connector assembly of claim 3 wherein said neck assembly includes a front wall with a hole therein and said wedge has a protrusion protruding from a front end thereof and receivable in said hole whereby said wedge can be removed from said space by pushing on said protrusion.

20. The connector assembly of claim 3 wherein said neck assembly includes a back wall with an opening therein in registry with said space and said wedge has an integral plug formation on the rear end there of receivable in and closing said opening.

21. The connector assembly of claim 1 wherein said resilient conductive means comprises a plurality of blocks of an electrically conductive elastomeric material, spaced apart and axially arranged, each with a hole therethrough through which the proximal end of said pacing lead can be easily inserted when said urging means are removed from said neck assembly thereby to position each of said connector bands on said pacing lead within one of said holes of one of said blocks after which said urging means can be inserted in said assembly to urge said blocks of conductive elastic material against said respective connector bands.

22. The connector assembly of claim 21 including a pluralty of insulated feedthrough members, each positioned within an opening in said top wall of said pacer case, and a wire conductor extending through each one of said insulated feedthroughs and being embedded at one end in one of said blocks of conductive elastomeric material and being connected at the other end to electronic control and pulse generating circuitry within said pacer case thereby providing continuity between each of said blocks and said control and pulse generating circuitry.

23. A method for connecting a pacing lead proximal end portion to a connector assembly of a cardiac pacer including a pacer case having a top wall and pulse generating means enclosed within said pacer case, said lead having a distal end portion and a proximal end portion with a plurality of connector bands mounted on said proximal end portion, an elastomeric neck mounted on said top wall of said pacer case, said neck having a lumen therein to receive said proximal end portion of said pacing lead, said connector assembly including a plurality of resilient conductive means adjacent to said lumen in said neck, and said neck assembly including removable means for urging said resilient conductor means against said connector bands, said method including the steps of:
 (a) removing said urging means from a space in said neck assembly above said elastomeric neck;
 (b) inserting said proximal end of said pacing lead into said lumen until said connector bands are in registry with said respective resilient conductive means; and
 (c) inserting said urging means through an opening in said neck assembly into said space in said neck assembly to urge said resilient conductive means against said connector bands.

24. The method of claim 23 including the further step of plugging the hole in said neck assembly.

* * * * *